(12) United States Patent
Sutterlin et al.

(10) Patent No.: US 7,722,613 B2
(45) Date of Patent: May 25, 2010

(54) SYSTEMS AND METHODS FOR REMOVING BODY TISSUE

(75) Inventors: Chester Sutterlin, Gainesville, FL (US);
Jason Blain, San Diego, CA (US);
Matthew Curran, Carlsbad, CA (US);
Troy Woolley, San Diego, CA (US);
Eric Kovach, Carlsbad, CA (US)

(73) Assignee: NuVasive, Inc., San Diego, CA (US)

( * ) Notice: Subject to any disclaimer, the term of this patent is extended or adjusted under 35 U.S.C. 154(b) by 174 days.

(21) Appl. No.: 10/527,538

(22) PCT Filed: Sep. 11, 2002

(86) PCT No.: PCT/US02/28926
§ 371 (c)(1),
(2), (4) Date: Mar. 11, 2005

(87) PCT Pub. No.: WO2004/024005
PCT Pub. Date: Mar. 25, 2004

(65) Prior Publication Data
US 2006/0074425 A1 Apr. 6, 2006

(51) Int. Cl.
*A61B 17/00* (2006.01)
(52) U.S. Cl. ............................................. 606/79; 606/80
(58) Field of Classification Search .................. 606/79, 606/80, 81
See application file for complete search history.

(56) References Cited

U.S. PATENT DOCUMENTS

| 4,108,162 | A |   | 8/1978  | Chikashige et al. |
|-----------|---|---|---------|-------------------|
| 4,633,542 | A | * | 1/1987  | Taravel ....................... 15/167.1 |
| 5,190,548 | A | * | 3/1993  | Davis ........................... 606/80 |
| 5,355,547 | A |   | 10/1994 | Fitjer |
| 5,445,164 | A | * | 8/1995  | Worthen et al. ............. 600/572 |
| 5,573,547 | A | * | 11/1996 | LeVeen et al. .............. 606/232 |
| 5,733,288 | A | * | 3/1998  | Allen ........................... 606/79 |
| 5,795,291 | A | * | 8/1998  | Koros et al. ................. 600/232 |
| 5,899,850 | A | * | 5/1999  | Ouchi ......................... 600/104 |
| 6,083,228 | A |   | 7/2000  | Michelson |
| 6,099,309 | A |   | 8/2000  | Cardarelli |
| 6,127,597 | A |   | 10/2000 | Beyar et al. |
| 6,210,377 | B1| * | 4/2001  | Ouchi ......................... 604/264 |
| 6,423,078 | B1|   | 7/2002  | Bays et al. |
| 6,440,138 | B1| * | 8/2002  | Reiley et al. .................. 606/79 |

* cited by examiner

*Primary Examiner*—Eduardo C Robert
*Assistant Examiner*—Mary Hoffman
(74) *Attorney, Agent, or Firm*—Jonathan Spangler

(57) ABSTRACT

Devices and methods for removing body tissue involving the use of a brush member (12) having a plurality of bristle members defining a capacity for carrying body tissue. The brush member (12) is capable of being manipulated within said body to thereby receive body tissue within said brush member (12) such that said body tissue may be carried and thereafter removed from said body. Also provided are protective devices (90) dimensioned to be positioned near an entrance into the target site, the protective devices (90) for establishing a barrier between the brush member (12) and at least a portion of the body tissue adjacent to the entrance. The protective devices (16) may comprise one of a cannula assembly (14) and a retractor assembly.

11 Claims, 20 Drawing Sheets

SYSTEMS AND METHODS FOR REMOVING BODY TISSUE

CROSS-REFERENCE TO RELATED APPLICATION

This application claims the benefit of the filing date under 35 USC §120 or 365(c) of PCT Application entitled "Systems and Methods for Removing Body Tissue," Application No. PCT/US02/28926, filed Sep. 11, 2002, the entire contents of which are hereby expressly incorporated by reference into this disclosure as if set forth fully herein.

BACKGROUND OF THE INVENTION

I. Field of the Invention

This invention relates to devices and methods for removing body tissue. More particularly, the present invention relates to devices and methods for removing body tissue involving the use of a brush or brush-like element capable of collecting, carrying, or otherwise receiving body tissue for removal.

II. Discussion of the Prior Art

A large variety of pathologies affecting many different body tissues indicate the use of tissue ablation (i.e., removal or destruction of a tissue). Examples of such procedures include knee meniscectomy, knee synovectomy, chondromalacia and tears, loose body debridement, lateral retinacular release, plica removal, ligament and tendon release, contouring and sculpting of articular surfaces, debridement of inflamed synovial tissue, capsulectomy in the knee, complete or partial resection of internal organs, tumors and lesions.

Tissue ablation can be accomplished using many different ways, the two main categories consisting of mechanical and energy focusing means. Mechanical tools are used to cut away the targeted tissue. Thermal energy has also been used which heats the targeted tissue until the cells die. Lasers, radiofrequency waves, microwaves, ultrasound, and cryotherapy have all been used in thermal techniques. In a related technique, an electrical current is used to excite a fluid, creating a plasma layer. The highly energized plasma layer then incrementally disintegrates layers of the tissue.

The existing techniques suffer from a host of disadvantages. Typically, mechanical devices are small and remove tissue in very small increments. As a result, when large amounts of tissue must be removed the excision time may be exorbitant. The energy focusing techniques, in addition to suffering from the time disadvantage of the mechanical devices, are further limited. The energy levels applied to the tissue must be conservatively regulated to avoid damaging tissue beyond the targeted tissue.

One procedure, in particular, that is hindered by the existing devices and techniques is a spinal discectomy (i.e., removal of intervertebral disc material). Each disk is composed of an annulus fibrosus, a nucleus pulposus, and a pair of end caps which couple the annulus fibrosus and nucleus pulposus. The annulus fibrosus is an annular multi-layered composite structure. Each layer is constructed of fibrous tissue and fibrocartilage with the fibers of each layer ordered and oriented generally in the same direction. The fibers of adjacent layers pass in opposite directions so that when the layers are combined they create a mesh of concentric rings. The central cavity of the annulus houses the nucleus pulposus, which is a semi-gelatinous, highly elastic material. The final components are end caps constructed of thin layers of hyaline cartilage that cover both the top and bottom of each spinal disk. The end caps cover both the annulus fibrosus and the nucleus pulposus and assure that the nucleus pulposus remains within the confines of the annulus fibrosus.

Oftentimes, disks become herniated, or bulge, due to structural damage to the annulus fibrosus. The bulging disk may place pressure on nearby nerves, which can lead to debilitating pain, numbness or muscle weakness. Treatments used to reduce the affects of a damaged disk range from bed rest to spinal fusion. Due to the major shortcomings of those extreme treatments they are often not desirable. A discectomy, either full or partial, can help to balance the burdens and benefits of bed rest and fusion or help prepare the intervertebral site for procedures like fusion.

When a partial discectomy is performed, a portion of the nucleus pulposus of a herniated disc is excised. Partially removing the nucleus material can reduce the pressure exerted by the nucleus on the annulus and reduce the bulging. In this procedure, the surgeon must first make an appropriate incision through the skin and other tissue layers, and then typically create an access hole through the herniated annulus (i.e., an annulotomy) to treat the offending tissue. Such access holes are created with a variety of surgical instruments including scalpels, probes, trephines, etc., and the access hole may range in size from 3 to 6 mm in diameter.

Upon entry into the interior annular space, the surgeon removes the offending tissue. The tools typically used are only able to remove small portions of tissue with each approach. As a result, removal of the tissue during a discectomy can take an exorbitant amount of time. In addition, in some cases, when ablation of the verterbral body surfaces adjacent to the disc is required, an additional tool must be used adding additional time and steps to the procedure. The additional time requirement of this procedure gives rise to a need for tools and methods for performing rapid discectomy and end plate ablation.

The present invention is directed at addressing this need and eliminating, or at least reducing, the effects of the shortcomings of the prior art systems as described above.

SUMMARY OF THE INVENTION

The present invention overcomes the drawbacks of the prior art by providing, according to a first broad aspect of the present invention, a device for removing body tissue comprising a brush member dimensioned for introduction into a body. The brush member has a plurality of bristle members defining a capacity for carrying body tissue. The brush member is capable of being manipulated within the body to thereby receive body tissue within the brush member such that the body tissue may be carried and thereafter removed from the body.

In a further aspect of this device, the capacity for carrying body tissue is defined by at least one of the space between the bristle members and the space between groupings of the bristle members. The bristle members may be grouped to define at least one generally helical space for receiving and carrying body tissue therein, at least one generally axial space for receiving and carrying body tissue therein, and/or at least one generally arcuate space for receiving and carrying body tissue therein.

In another aspect, the bristle members may be disposed in a generally solid configuration with spacing sufficient to receive and carry body tissue between said bristle members. In a further aspect, the brush member has at least one of a generally cylindrical, generally elliptical, and generally polygonal cross-sectional shape. The bristle members may comprise one of metal and plastic and, more particularly, at least one of stainless steel wire, carbon-tempered steel wire, non-ferrous wire, and synthetic wire. The bristle members may be generally cylindrical in cross-section with a diameter from 0.002 to 0.100 inches.

According to certain aspects, the brush member may be generally cylindrical with a diameter from 0.082 to 1.225 inches. The brush member may also include a stem member extending therefrom for use in manipulating the brush member within said body. In a further aspect, the stem member may be generally cylindrical with a diameter from 0.125 to 0.250 inches. The stem member may also be equipped with a quick-connect coupling for engaging with at least one of a handle member and an extension member. In a further aspect, at least a portion of the bristle members may be retractable within the stem member. The stem member may have a length of from 1 to 24 inches and may include depth indicia.

Among the host of possible applications, the brush member may, according to a further broad aspect, be dimensioned to be introduced into an intervertebral space to receive, carry, and remove intervertebral disc material. In particular, the brush member may be used to remove intervertebral disc material in order to thereafter introduce a spinal implant into the intervertebral space. In another related aspect, the brush member may be dimensioned to be introduced into a vertebral body to receive, carry, and remove osseous material.

The present invention overcomes the drawbacks of the prior art by providing, according to a second broad aspect of the present invention, a system for removing body tissue comprising a brush member of the type described above in combination with a protector dimensioned to be positioned near an entrance into a target site. The protector establishes a barrier between the brush member and at least a portion of the body tissue adjacent to the entrance. The brush member and protector may be employed to remove body tissue during at least one of a percutaneous surgical procedure and an open surgical procedure.

In one further aspect, the protector comprises a cannula dimensioned to extend to the entrance of the target site, wherein the cannula has an inner lumen dimensioned to slideably receive the brush member for passage into the target site. The cannula may include a handle member for directing the cannula to the entrance of the target site. In one aspect, the inner lumen of the cannula and the brush member have approximately the same cross-sectional shape According to a further embodiment, the brush member includes a stem member, and the system further includes a drive assembly capable of engaging with the stem member for manipulating the brush member within the target site. The drive assembly may comprise one of a powered drive assembly coupled to the stem member and a manual drive assembly coupled to the stem member. The powered drive assembly may comprise a power drill. The manual drive assembly may include a handle member capable of being coupled to the stem member and, in a further embodiment, may include an extension member coupled to the handle and a quick-connect coupling assembly for releasable connection to the stem member In either case (powered or manual), the drive assembly may include a stop member coupled to the stem member for controlling the depth to which the brush member can be advanced into the target site.

According to one aspect of the system, the body tissue adjacent to the entrance may include at least one of neural tissue, dura tissue, and vasculature adjacent to the spine. If so, the cannula may include a lip member at a distal end thereof dimensioned to retract at least one of the neural tissue, dura tissue, and vasculature.

In yet another aspect of the system of the present invention, the protector comprises a retractor having at least one blade member for establishing a barrier between the brush member and the body tissue adjacent to the entrance to the target site. The body tissue adjacent to the entrance may include at least one of neural tissue and dura tissue of the spine. If so, the retractor may includes a first blade member for retracting the neural tissue and a second blade member for retracting the dura tissue. The first blade member and second blade member may have a fixed or variable angle therebetween. In the latter case, the retractor may include a handle assembly for varying the angle between the first blade member and the second blade member.

Among the host of applications of the system of the present invention, the brush member may, according to a further broad aspect, be dimensioned to be introduced into the intervertebral space to receive, carry, and remove intervertebral disc material. In particular, the brush member may be used to remove intervertebral disc material in order to thereafter introduce a spinal implant into the intervertebral space. In another related aspect, the brush member may be dimensioned to be introduced into a vertebral body to receive, carry, and remove osseous material.

The present invention overcomes the drawbacks of the prior art by providing, according to a third broad aspect of the present invention, a method for removing body tissue, comprising the steps of: (a) creating a working channel from a patient's skin to a surgical target site (via percutaneous and/or open techniques); (b) inserting a brush member of the type set forth above into the surgical target site, the brush member having a plurality of bristle members defining a capacity for carrying body tissue; (c) manipulating the brush member within the body to receive body tissue within the brush member; and (d) removing the brush member from the surgical target site.

According to various aspects, the surgical target site may be an intervertebral disc space, and the step of inserting a brush member may include, prior to the step of inserting the brush member, positioning a protector near an entrance into the intervertebral disc space for establishing a barrier between the brush member and at least one of neural tissue, dura tissue, and vasculature adjacent to the entrance. The protector may comprise a cannula of the type described above and/or retractor (fixed or variable angle) of the type described above.

BRIEF DESCRIPTION OF THE DRAWINGS

Other objects and advantages of the invention will become apparent upon reading the following detailed description and upon reference to the drawings in which.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination.

The present invention overcomes the shortcomings of tissue ablation techniques of the prior art by employing a brush member having a plurality of bristle members defining a capacity for carrying body tissue. The capacity for carrying body tissue is based on the spacing between the individual bristle members and/or the spacing between one or more groups of bristle members. While the present invention is described below within the context of removing body tissue relating to the spine (i.e. intervertebral disc material and/or osseous material), it is to be readily appreciated that the present invention may be used in any number of different medical procedures. These may include, but are not necessarily limited to, knee meniscectomy, knee synovectomy, chondromalacia and tears, loose body debridement, lateral retinacular release, plica removal, ligament and tendon release, contouring and sculpting of articular surfaces, debridement of inflamed synovial tissue, capsulectomy in the knee, complete or partial resection of internal organs, tumors and lesions. As used herein, the term "body tissue" includes any tissue present in a living or dead body, including but not limited to tissue involved in the aforementioned list of medical procedures (including intervertebral disc material, cancellous and cortical bone, and fatty tissues).

Figure 1:
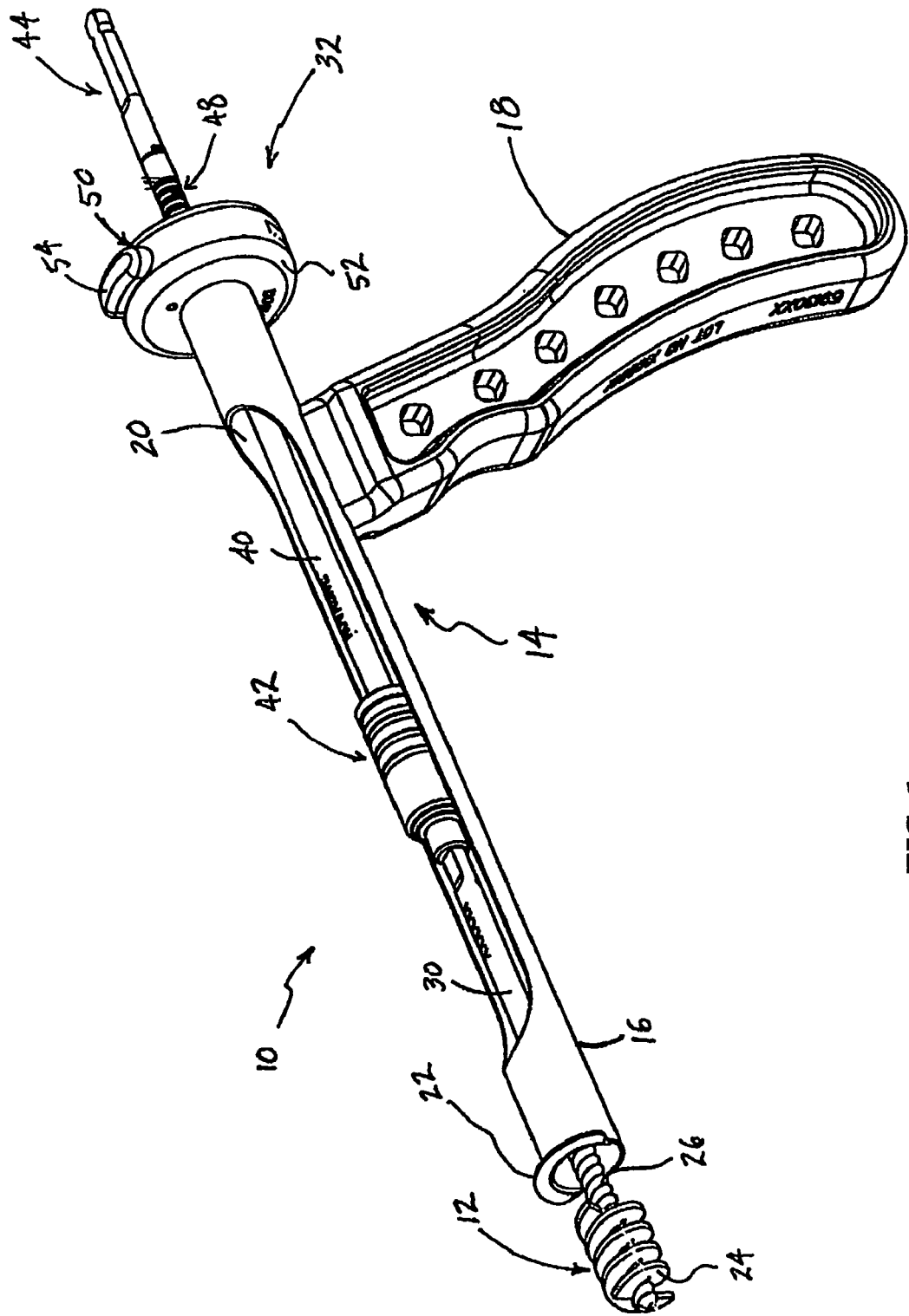
FIG. 1 is a perspective view of a system for removing body tissue according to one broad aspect of the present invention.

FIG. 1 illustrates a system 10 for removing body tissue according to a first broad aspect of the present invention. The system 10 includes a brush member 12 and a cannula assembly 14. Although described immediately below within the context of use with the cannula assembly 14, it is to be understood at the outset that the brush member 12 (including all the variations shown and described herein—and their equivalents) forms an independently patentable aspect of the present invention. As will be described in greater particularity below, this is based on the primary feature of providing the brush member 12 having a plurality of bristle members defining a capacity for carrying body tissue, wherein the brush member 12 is capable of being manipulated within the body to thereby receive body tissue within the brush member 12 such that the body tissue may be carried and thereafter removed from the body. The capacity for carrying body tissue is defined by at least one of the space between the individual bristle members forming the brush member 12 and the space between groupings of bristle members forming the brush member 12.

Figure 2:
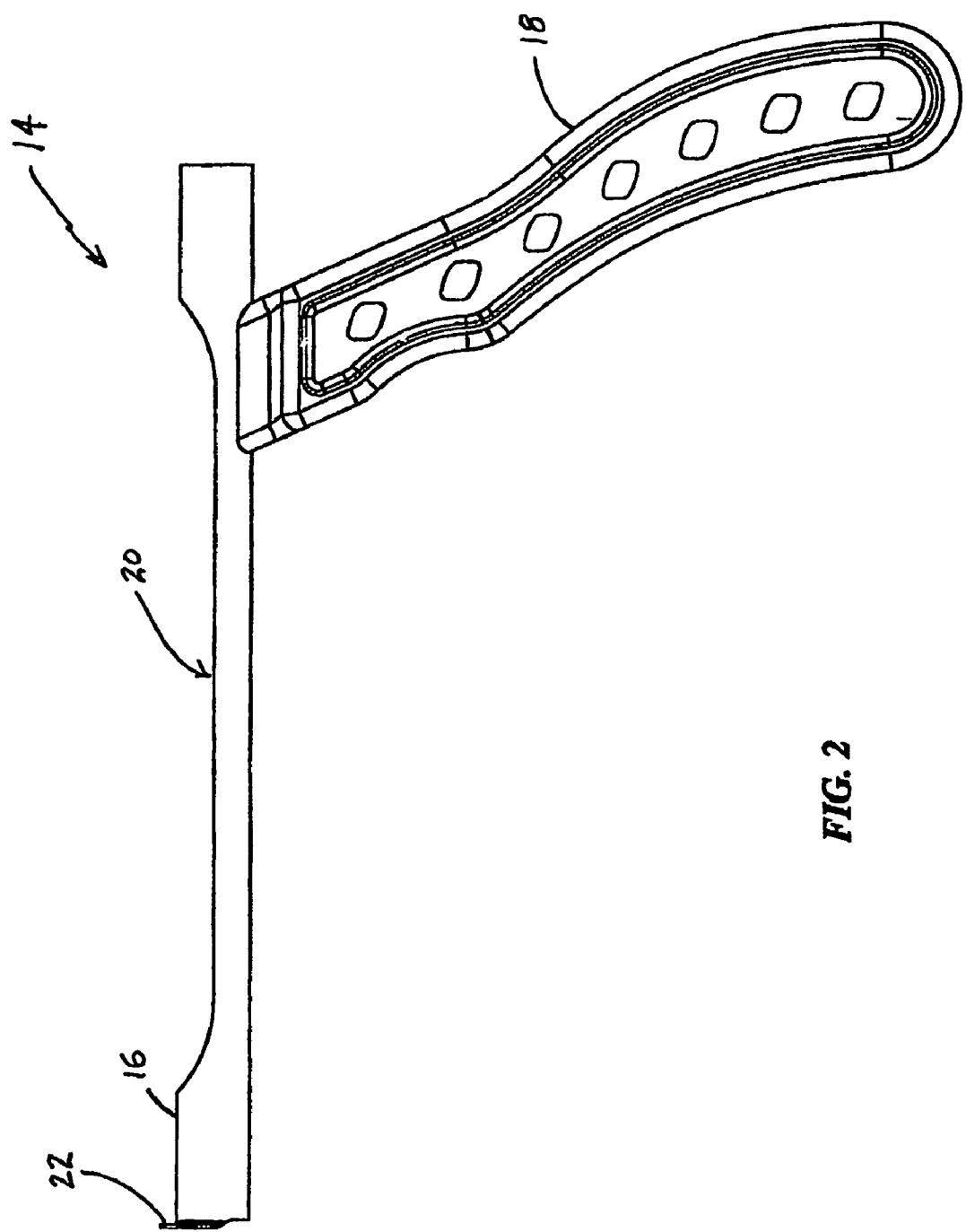
FIG. 2 is a side view of a cannula assembly forming part of the system for removing body tissue shown in FIG. 1.

With combined reference to FIGS. 1-2, the cannula assembly 14 includes a cannula member 16 and a handle member 18. The cannula member 16 has an inner lumen 20 dimensioned to pass the brush member 12 therethrough en route to a surgical target site within a body. In one aspect of the present invention, the surgical target site may be one of the intervertebral disc space and an intravertebral body space. Importantly, the distal end of the cannula member 16 (opposite the handle member 18) serves to form a protective barrier between the brush member 12 and tissues adjacent to the surgical target site. Within the context of spinal applications, such tissues may include, but are not necessarily limited to, neural structures (i.e. exiting nerve roots) and dura tissue (during posterior and/or postero-lateral access to the spine) and vasculature (during anterior access to the spine). To further protect against inadvertent contact with such adjacent tissues (including pinching such structures), the cannula assembly 14 is equipped a lip member 22 capable of preventing such tissues from migrating into the distal opening of the cannula 16.

Figures 3, 4:
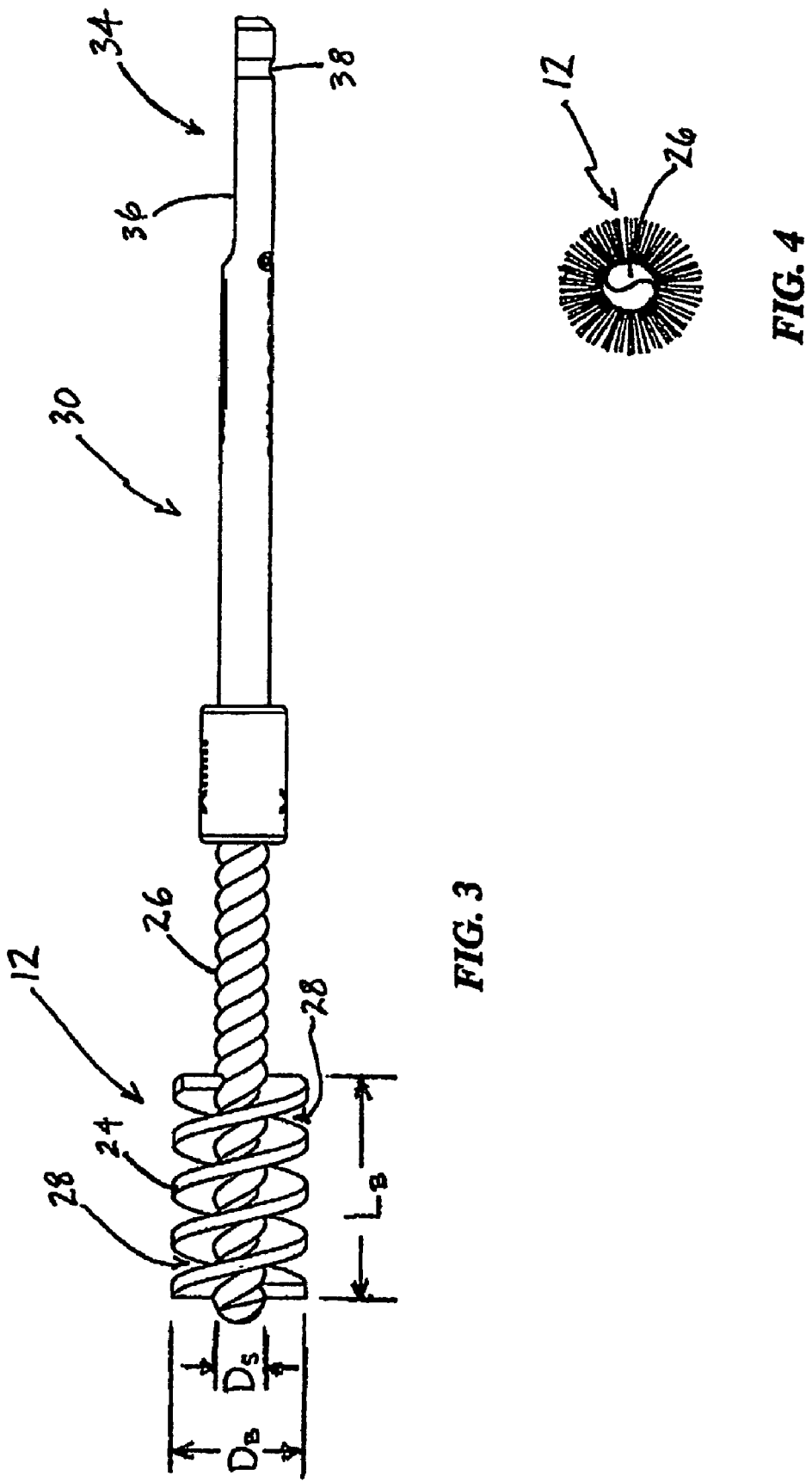
FIGS. 3 and 4 are side and end views, respectively, of a brush member and adapter member forming part of the tissue removal system of FIG. 1.

With reference to FIGS. 1 and 3-4, the brush member 12 is provided, by way of example only, having its bristles disposed in a dual spiral or helical grouping 24 along a stem member 26. This helical configuration 24 of the bristles creates a generally helical space 28 extending along the length ($L_B$) of the brush member 12. This helical space 28, along with the space between the individual bristles forming the helical grouping 24, defines a carrying capacity within the brush member 12 for the removal of body tissue. In a preferred embodiment, the length ($L_B$) of the brush member 12 may range from 0.25 to 4.0 inches and the diameter ($D_B$) of the brush member 12 may range from 0.082 to 1.225 inches.

The bristles may be constructed from a number of materials that have sufficient strength to avoid shedding or dislodging of the bristles from the stem 26 during use and of proven safety in medical applications. Such bristle materials may include, by way of example, metal and plastic and, more particularly, stainless steel wire, carbon-tempered steel wire, non-ferrous wire, and synthetic materials (such as nylon or other plastics). In a preferred embodiment, the individual bristles are generally cylindrical, each having a diameter ranging from 0.002 to 0.100 inches. Although not shown, the bristles may also be provided having a square or other polygonal cross-section (depending on the method of manufacture - which may include drawing, extrusion or molding) without departing from the scope of the present invention.

The stem member 26 is a generally rigid member that extends, according to one embodiment, away from the brush member 12 for connection to a quick-connect adapter 30. The stem member 26 may be provided having a diameter ($D_S$) ranging from 0.125 to 0.250 inches and a length ranging from 1 to 24 inches. The quick-connect adapter 30 enables the stem member 26 to be quickly coupled or de-coupled from a manual drive assembly 32 to be described below. The quick connect adapter 30 is generally cylindrical with a connector portion 34 on its proximal end. The distal end of the quick connect adapter 30 may be coupled to the stem member 26 by crimping or by any mechanical connection that provides sufficient strength to withstand torsional forces during rotation of the brush member 12. The male connector portion 34 includes a flat surface 34 that provides a bearing surface that transmits rotation between the brush member 12 and the manual drive assembly 32, and a concentric channel 53 that is engaged by a retractable feature in a mating device that prevents axial movement between the quick connect adapter 30 and the a mating device. It should be appreciated that there are many known connection mechanisms that may be substituted without departing from the scope of the present invention, including but not limited to a Jacob's adapter.

Figure 5:
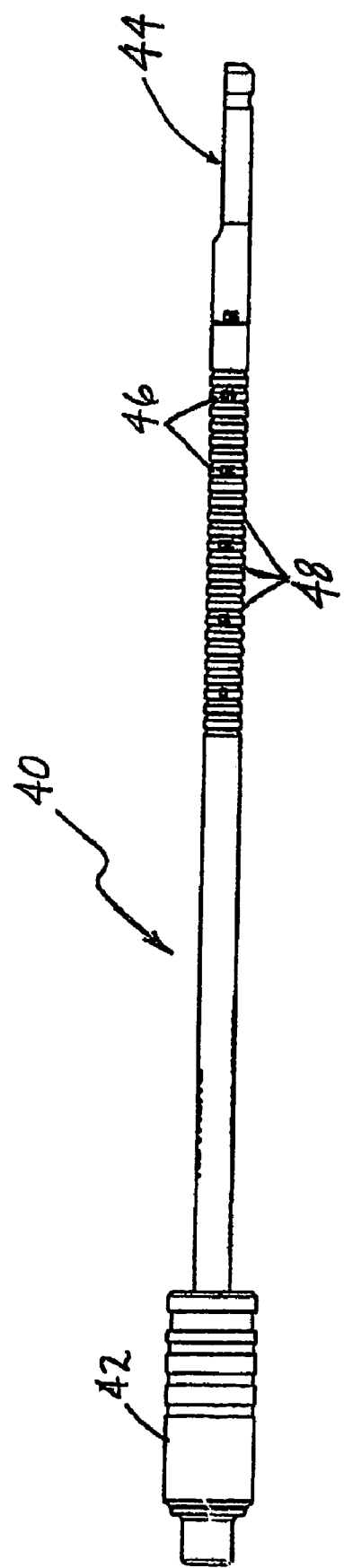
FIG. 5 is a side view of an extension member forming part of the tissue removal system shown in FIG. 1.

Turning to FIGS. 1 and 5, the manual drive assembly 32 includes, by way of example, an extension adapter 40 having a female quick-connect collet 42 at its distal end and a male connecting portion 44 at its proximal end. The female quick connect collet 42 is of known construction and functions to couple the extension adapter 40 to the quick-connect adapter 30. The male connecting portion 44 is of similar construction to the corresponding connecting portion 34 of the quick connect adapter 30 and, as such, need not be described again here, except to point out that the connecting portion 44 of the extension adapter 40 is, in a preferred embodiment, to be coupled to a manual handle (not shown) such that a surgeon may impart rotational force on the brush member 12 to effectuate the tissue removal of the present invention. According to an alternate embodiment, the connecting portion 44 may be coupled to a power drill (thus forming a powered drive mechanism according to the present invention).

Figure 6:
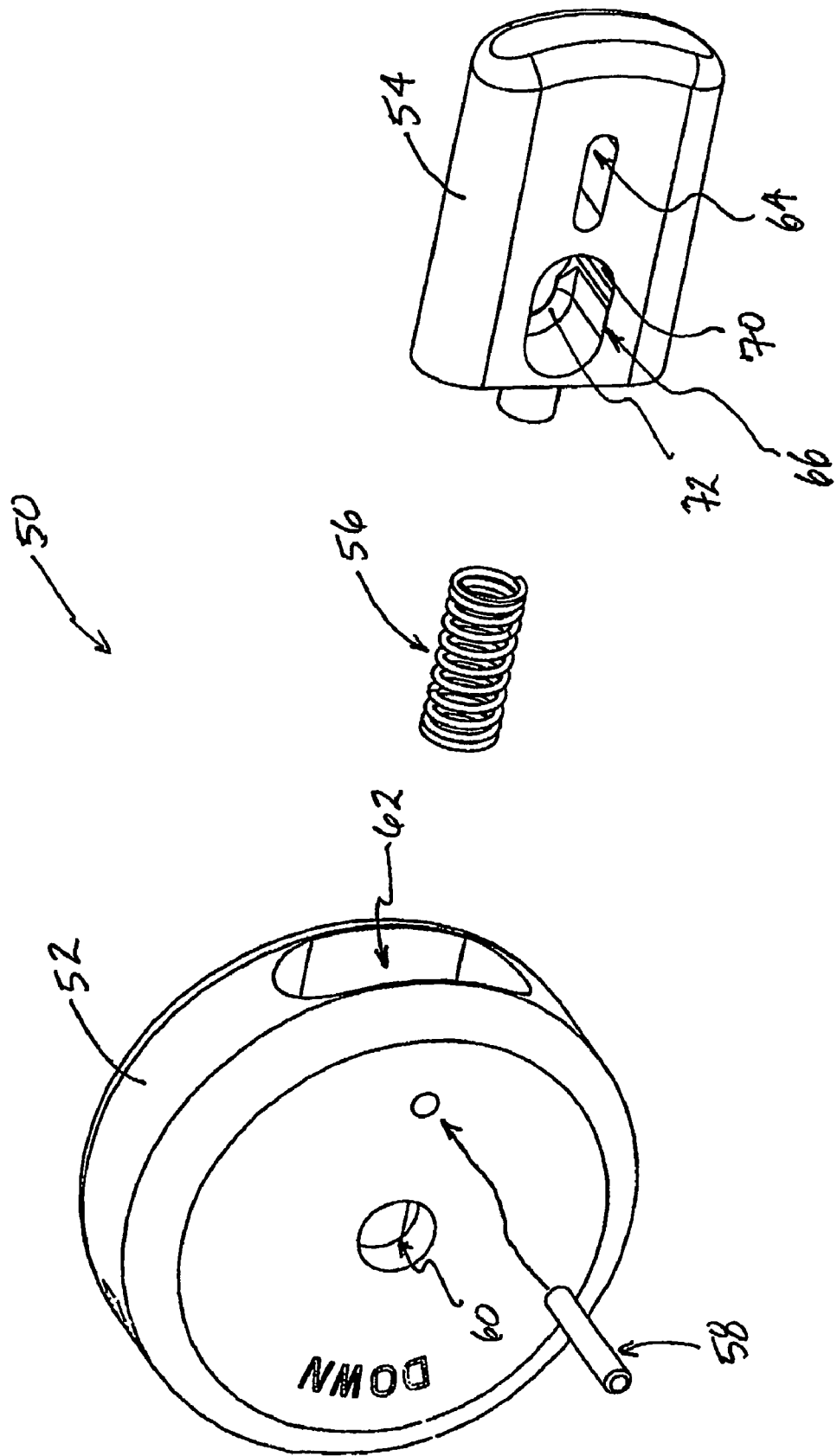
FIGS. 6 and 7 are perspective and cross-sectional views, respectively, of a stopper assembly forming part of the tissue removal system shown in FIG. 1.
Figure 7:
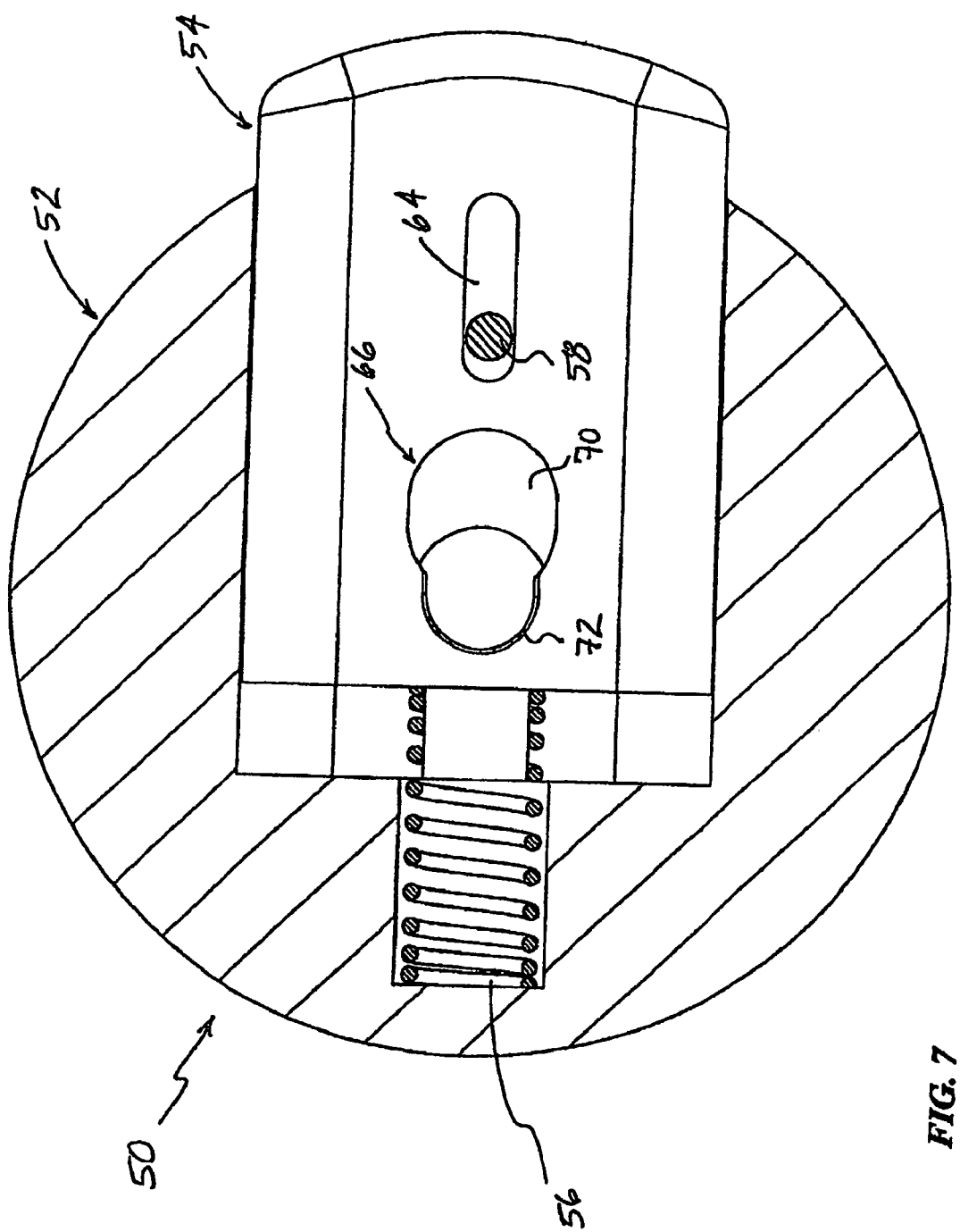

The extension adapter 40 may be provided with certain depth management features to control or manage the extent to which the brush member 12 is introduced into the target surgical site. In one embodiment, these depth management features may include indicia 46 disposed along the length of the extension adapter 40 (denoting, by way of example, a depth ranging from 0 to 50 mm) and a plurality of notches 48. These depth management features are particularly suited for use with a stopper assembly 50 shown generally in FIG. 1 and in detail in FIGS. 6-7.

The stopper assembly 50 includes a stop member 52, a detent member 54, a spring 56, and a locking pin 58. The stop member 52 includes an aperture 60 dimensioned to receive the extension member 40, as well as a side aperture 62 for receiving the detent member 54. The detent member 54 includes a locking pin slot 64, an engagement aperture 66, and an extension 68. The slot 64 allows the locking pin 58 to travel therein to control the inward and outward travel of the detent member 54 within the stop member 52. The aperture 66 includes an enlarged region 70 and an engagement ridge 72 (hence the "semi-constrained" terminology). When the detent 54 is pushed into the stop member 52 (by urging against the spring 56), the enlarged region 70 is moved into general coaxial alignment with the aperture 60 such that the extension adapter 40 may be passed through the stop member 52. Once positioned at a desired location along the notched region 48 of the extension adapter 40, the detent member 54 may be released such that the engagement ridge 72 will be disposed within one of the notches 48 and thereby restrict the movement of the extension adapter 40 relative to the stop member 52. In a preferred embodiment, the stop member 52 does not restrict either rotation of the brush member 12 or translation in the proximal direction. As a result, the brush member 12 is limited to a depth that can be predetermined while still allowing rotation and limited back and forth motion.

Figure 8:
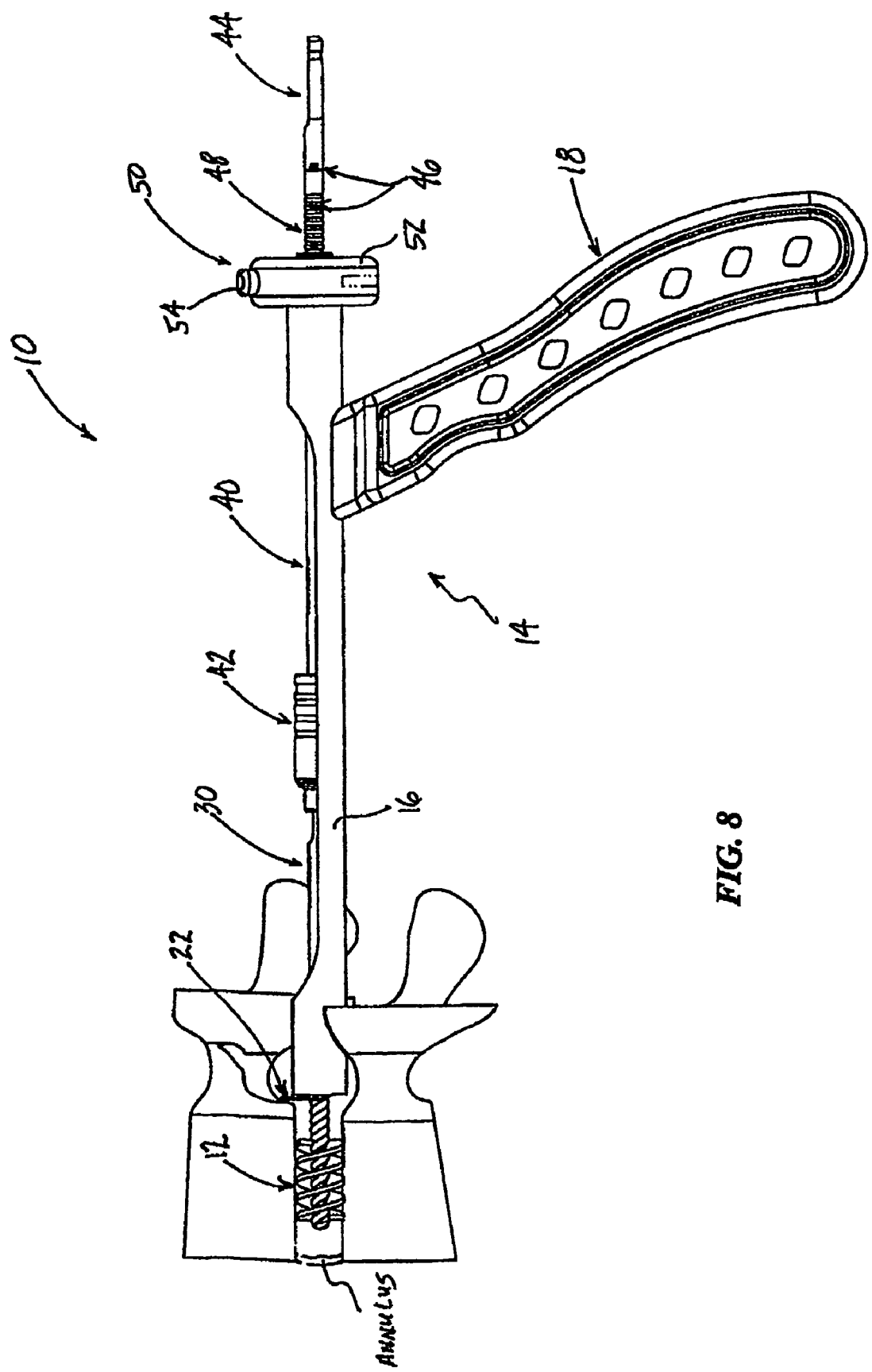
FIGS. 8 and 9 are side and top views, respectively, of the tissue removal system of FIG. 1 in use performing a discectomy.
Figure 9:
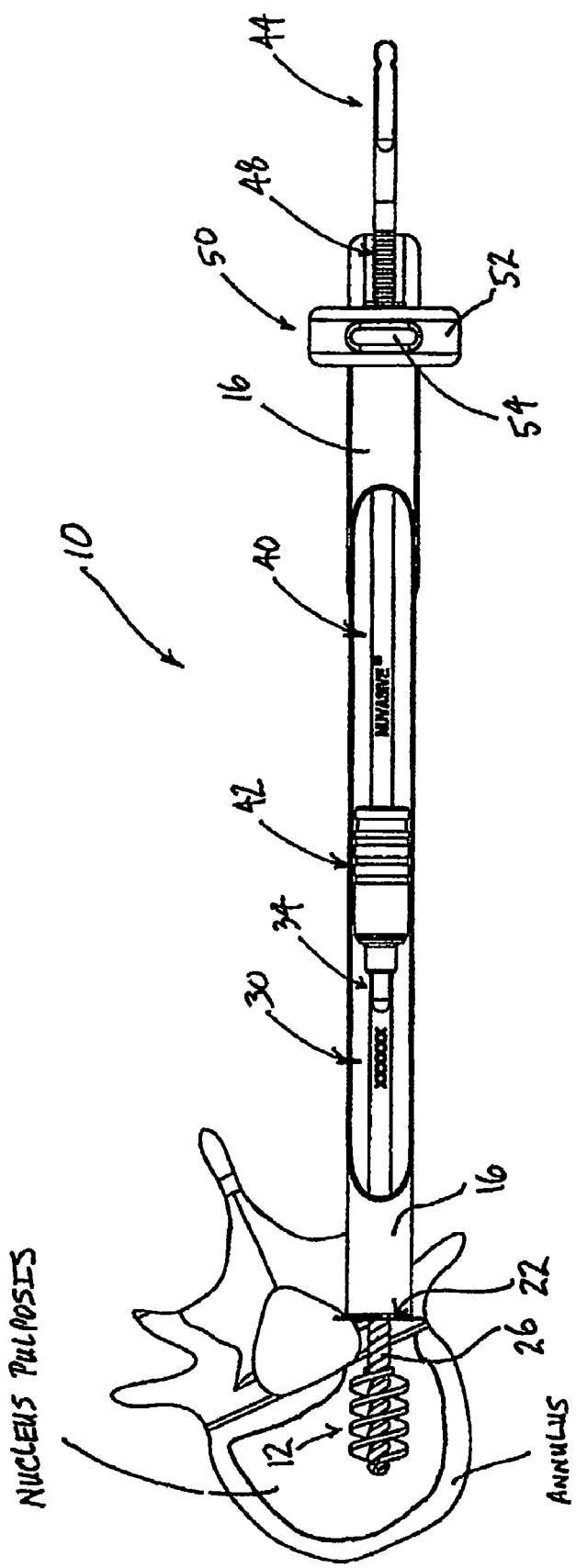

With reference to FIGS. 8-9, the tissue removal system 10 will now be described, by way of example only, in use within in the context of a discectomy procedure despite its general utility in any of a variety of tissue removal procedures. First, a working channel is formed between the patient's skin and the surgical target site, which in this case is an intervertebral disc space. The working channel be created via a traditional "open" techniques or a percutaneous or "minimal access" technique. With the working channel created, the cannula 16 may be inserted such that its distal end (with the lip member 22) is disposed adjacent to or in the generally proximity of the annulus. In a preferred embodiment, the lip member 22 may be used to prevent any surrounding tissue (such as exiting nerve roots and/or dura tissue in the case of the posterolateral approach shown best in FIG. 9) from migrating into the distal opening of the cannula 16. An annulotomy device of known construction may be extended to the disc through the cannula 16 to remove a section of the disc annulus.

Thereafter, the discectomy brush 12 may be extended into the disc nucleus via the cannula 16 and disc annulus. The brush member 12 may then be rotated, manually or by power means such as a drill, to remove disc material. Depending on the diameter of the brush member 12 and the distance between the adjacent vertebrae, the discectomy brush 12 may be used to remove tissue as well as ablate or partially decorticate the surfaces of the adjacent vertebrae. The brush member 12 may then be removed and may be discarded or cleaned depending on the brush material. In one embodiment, the brush is comprised of plastic and another of stainless steel.

After removal of such disc material and, optionally, preparation of the vertebral endplates, any of a variety of spinal implants may be inserted into the space created by the discectomy brush. These spinal implants may include, but are not necessarily limited to, allograft products, ceramic spacers, and total disc replacement devices. Whatever the implant, it should ideally be inserted into this space via the cannula 16. The annulus opening may then be closed (through any known means, such as sutures or patch devices or sealing compounds) and then the cannula 16 removed. It should be readily understood that anterior, extreme lateral, posterolateral or posterior approaches may be utilized using the principles of the present invention.

Figure 10:
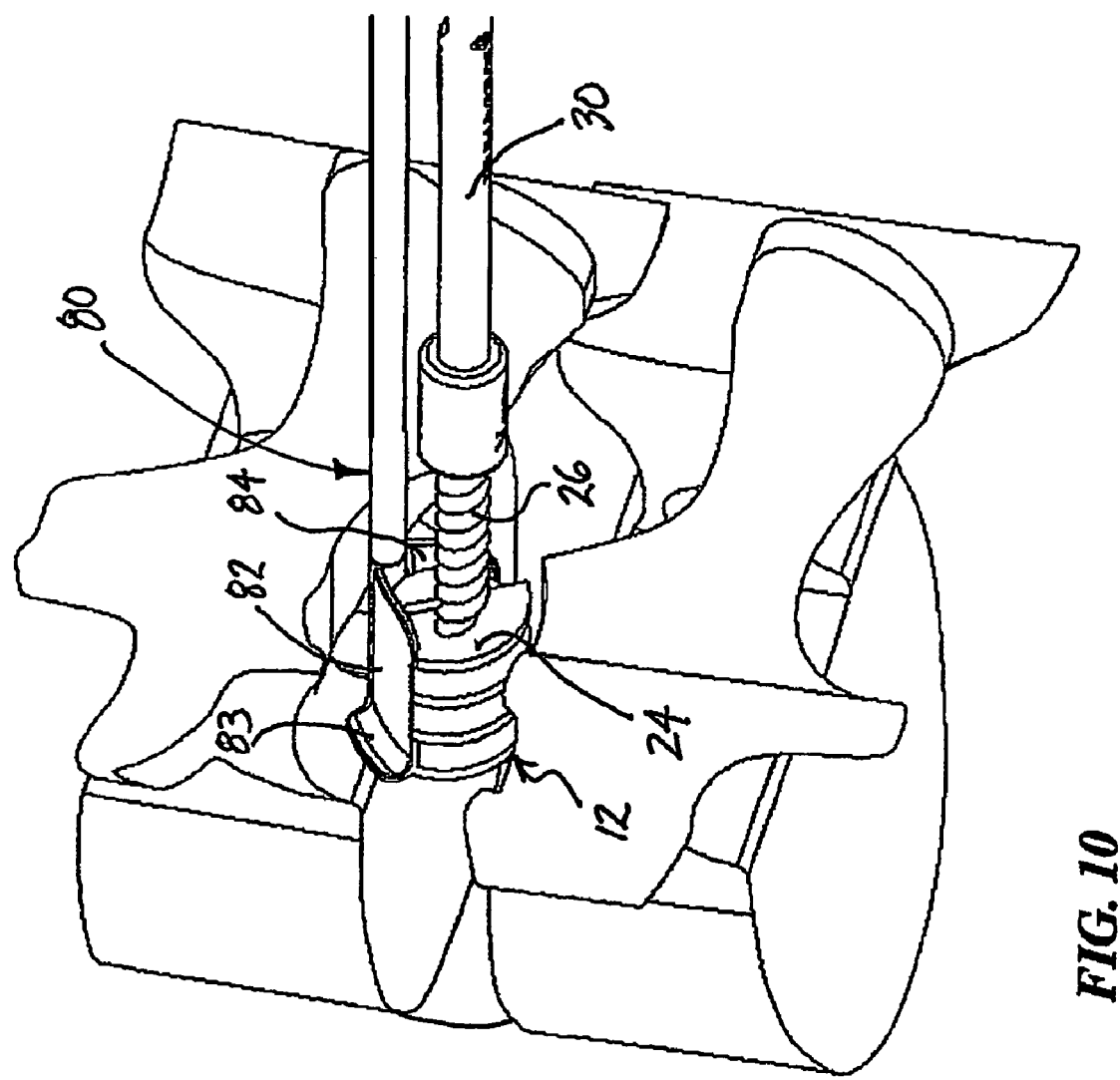
FIGS. 10 and 11 are perspective and side views, respectively, of a retractor forming an alternate aspect of the tissue removal system shown in FIG. 1 (without the cannula assembly 14)
Figure 11:
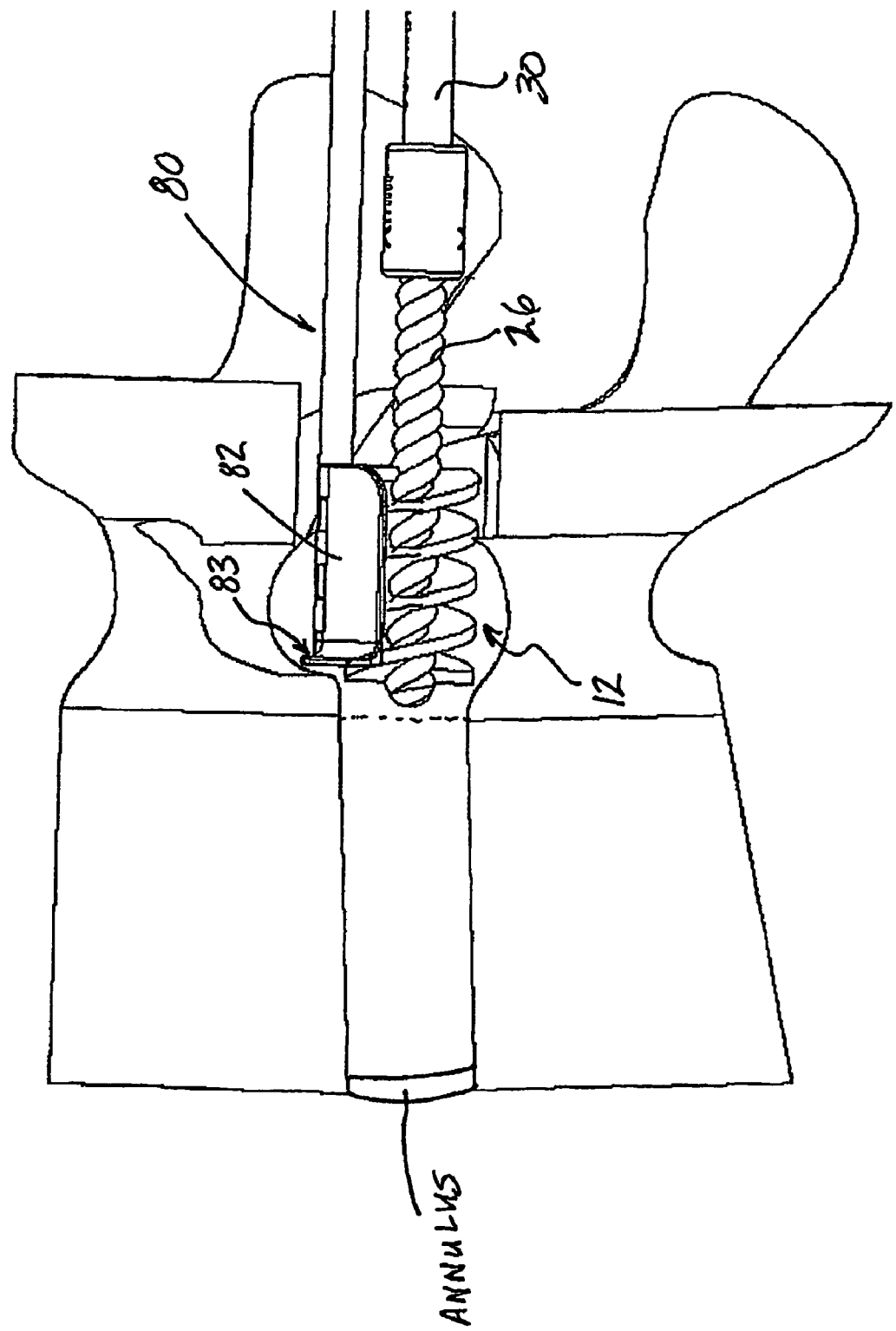
Figure 12:
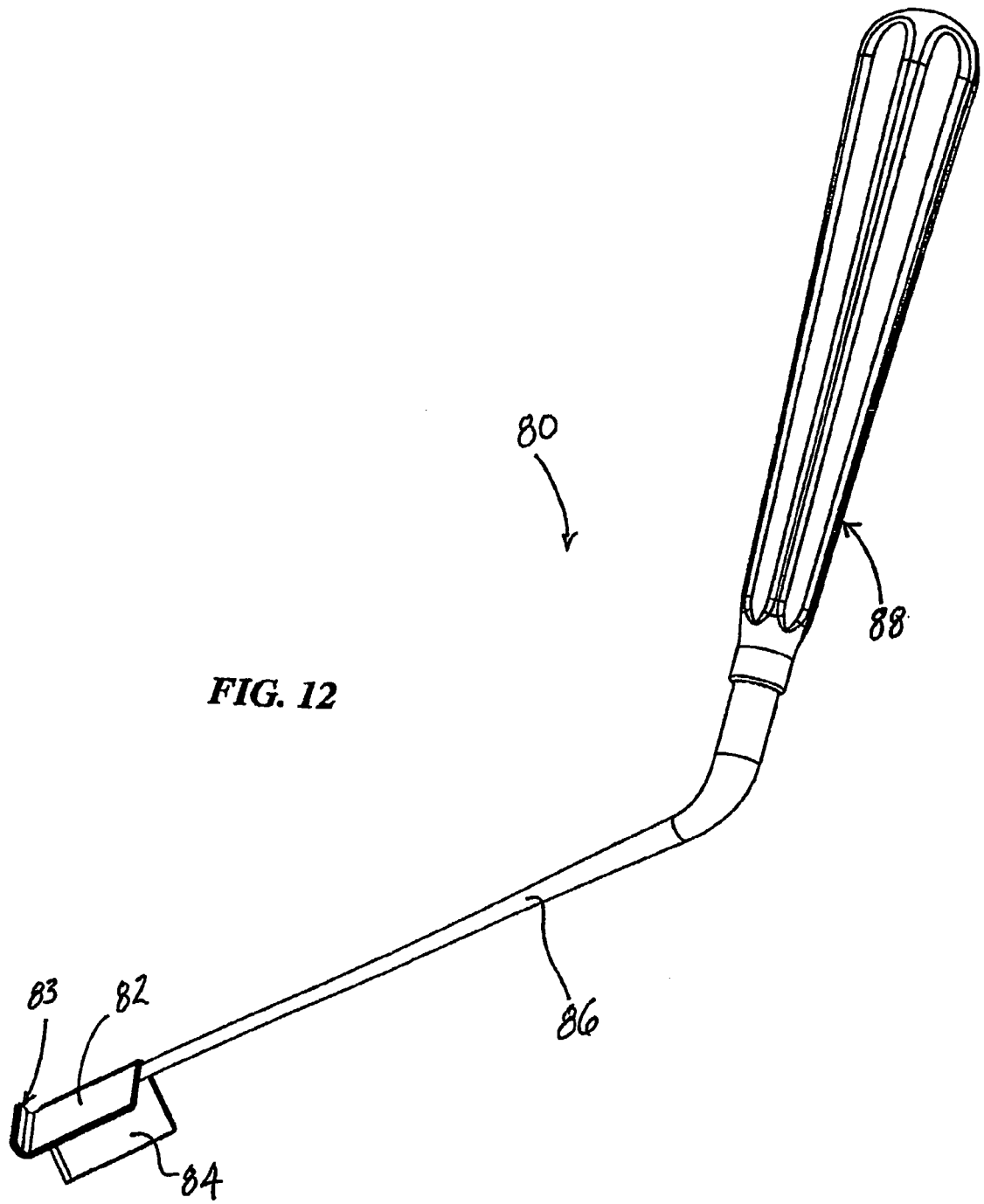
FIG. 12 is a perspective view of a fixed angle tissue retractor according to one embodiment of the present invention.

FIGS. 10-11 illustrate another broad aspect of the present invention, wherein a retractor 80 is provided (as opposed to the cannula assembly 16 described above) for the purpose of establishing a protective barrier between the brush member 12 and the tissues adjacent to the surgical target site (again, the intervertebral disc space). To accomplish this, the retractor 80 provides a pair of retractor blade 82, 84, which collectively form a generally "V" shaped construct capable of preventing the exiting nerve root (via blade 82) and the dura tissue (via blade 84) from migrating into a region that might otherwise result in the unwanted contact between the brush member 12 and these tissues. To facilitate this, each blade member 82, 84 is preferably equipped with a lip member 83 similar to lip member 22 of the cannula 16. As shown in FIG. 12, these blade members 82, 84 may be positioned relative to the surgical target site by virtue of an elongate curved shaft 86 coupled to a handle member 88. In one embodiment, the blade members 82, 84 have a fixed angle relative to one another ranging from between 50 and 75 degrees.

Figure 13:
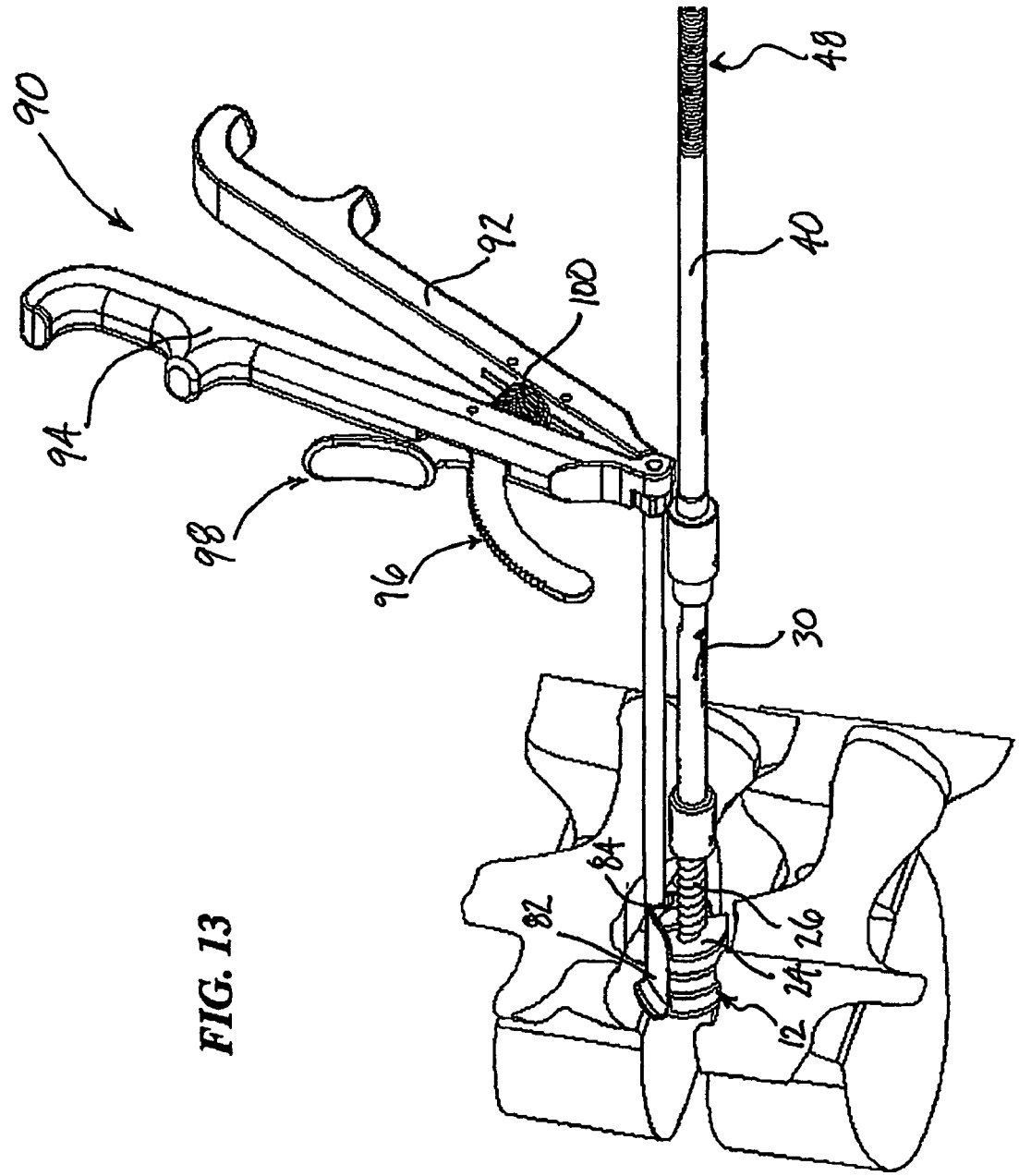
FIG. 13 is a perspective view of a variable angle tissue retractor according to further embodiment of the present invention.
Figure 14:
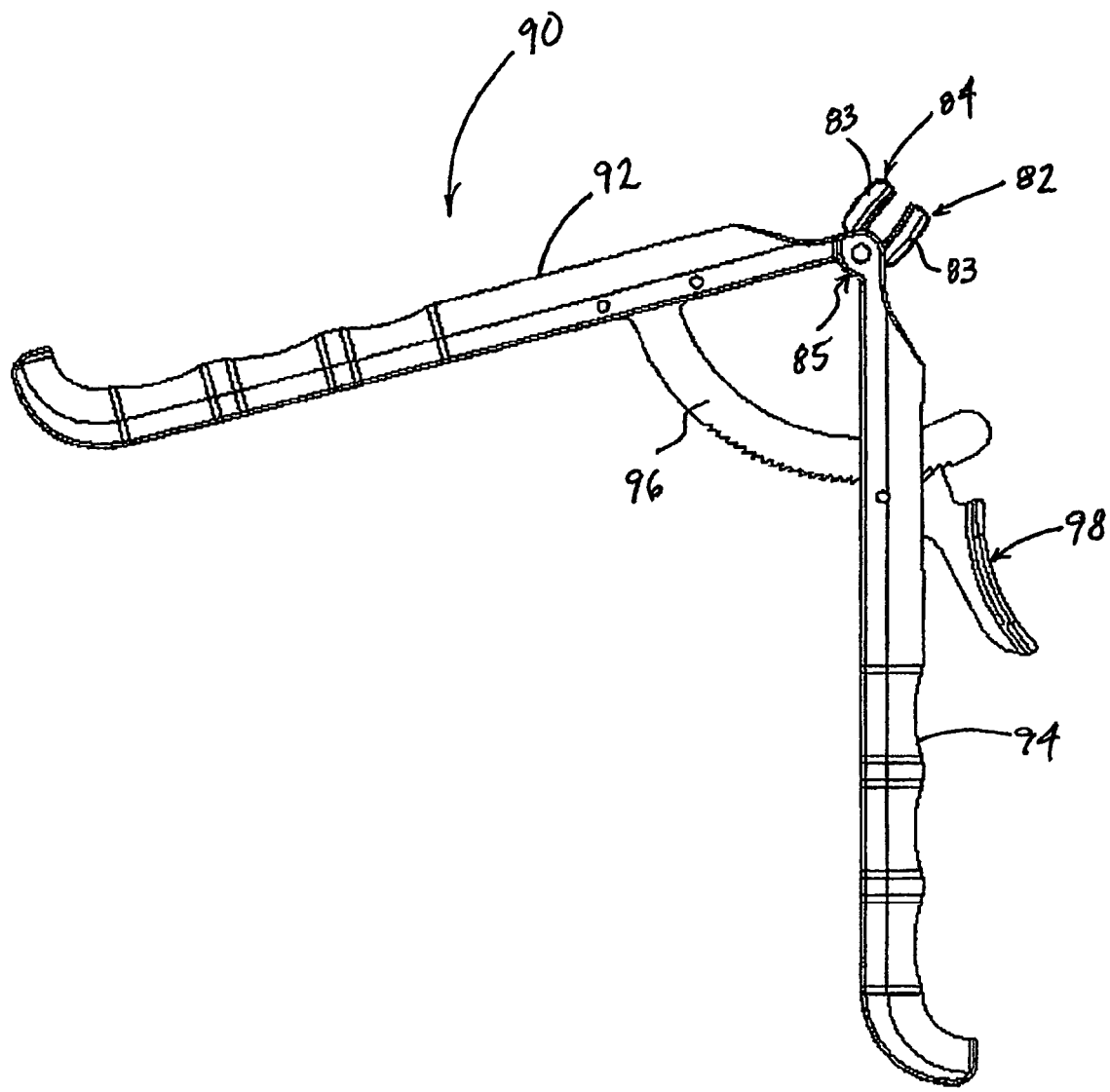
FIGS. 14 and 15 are top views showing the variable angle tissue retractor of FIG. 13 with the blade members generally closed (FIG. 14) and generally open (FIG. 15)
Figure 15:
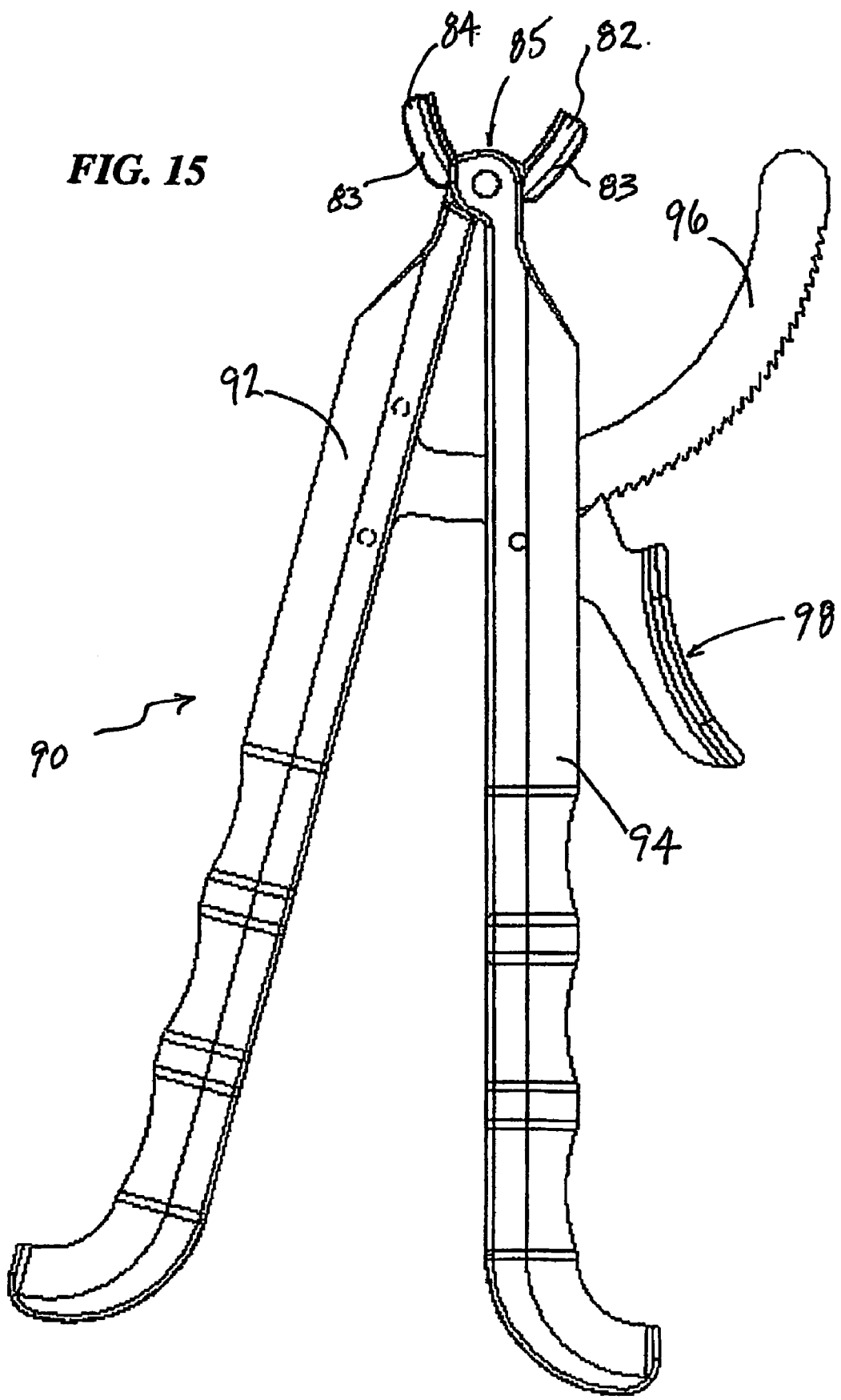

In an alternate embodiment shown in FIGS. 13-15, the retractor 80 may have blade members 82, 84 that are variable angle relative to one another. To accomplish this, a handle assembly 90 is provided having a pair of gripping elements 92, 94 which, upon manipulation towards (FIG. 14) and away (FIG. 15) from one another serve to increase and decrease, respectively, the angle between the blade members 82, 84. A shaft 85 extends between the gripping elements 92, 94 for independently coupling the blade members 82, 84 to one of the gripping elements 92, 94. A locking feature may be optionally be provided by equipping the first gripping element 92 with an arcuate, ribbed engagement element 96 which cooperates with a trigger member 98 coupled to the second gripping element 94. A spring 100 is disposed between the gripping elements 92, 94 and over a portion of the engagement element 96 to aid in the locking and unlocking of the handle assembly 90. In one embodiment, the angle between the blade members 82, 84 may be varied between 0 and 180 degrees and, more preferably, 0 to 90 degrees. The ability to close the angle between the blades 82, 84 (that is, to an angle of approximately 0 to 30 degrees) is helpful in that it may aid in placing the blades 82, 84 in proper position to form the barrier between the surrounding tissue and the brush member 12, such as by being introduced in the closed or reduced angle and thereafter opening the blades 82, 84 to thereby more gently move the adjacent structures aside.

Figure 16:
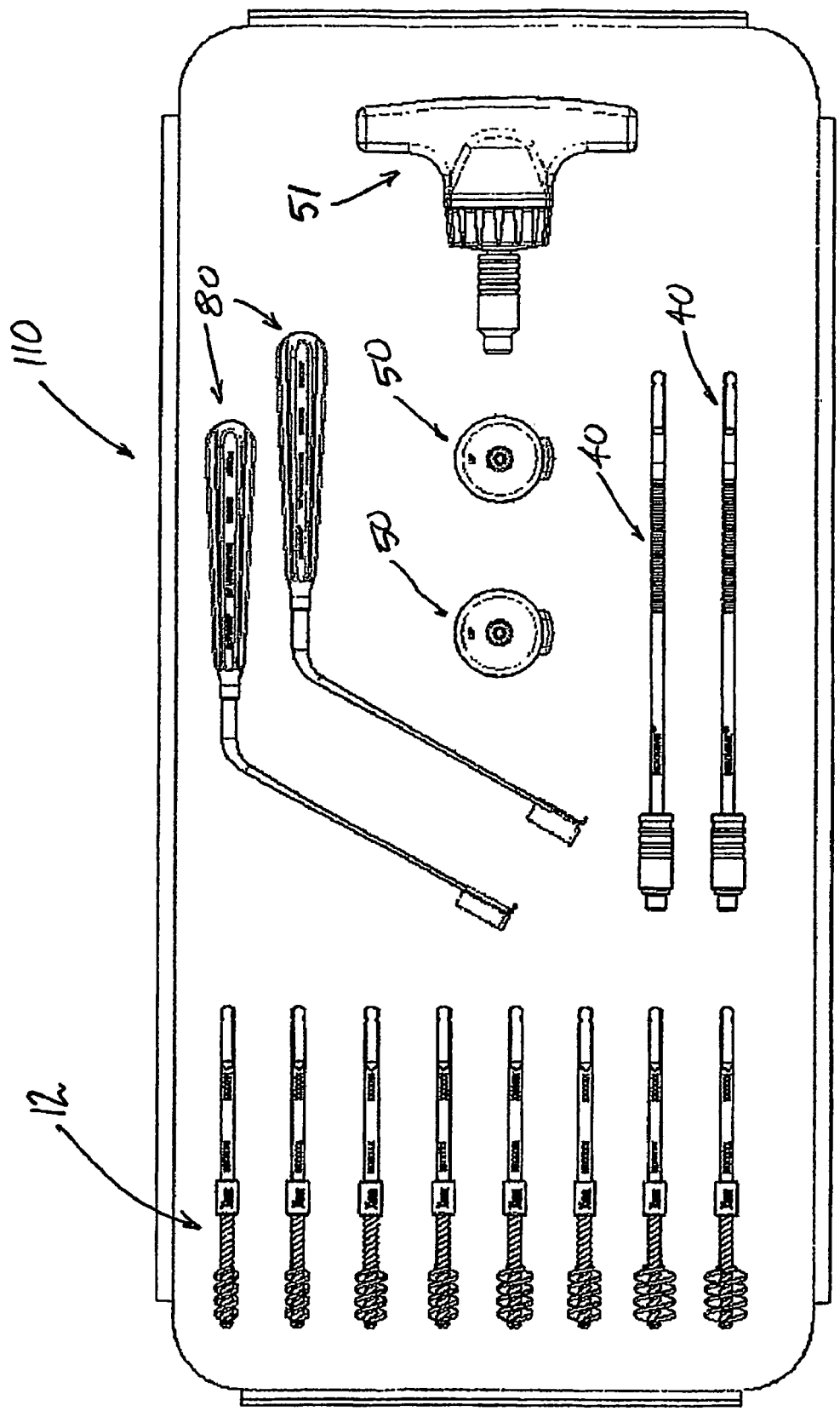
FIGS. 16 and 17 are top views of trays forming a kit according to one embodiment of the present invention.
Figure 17:
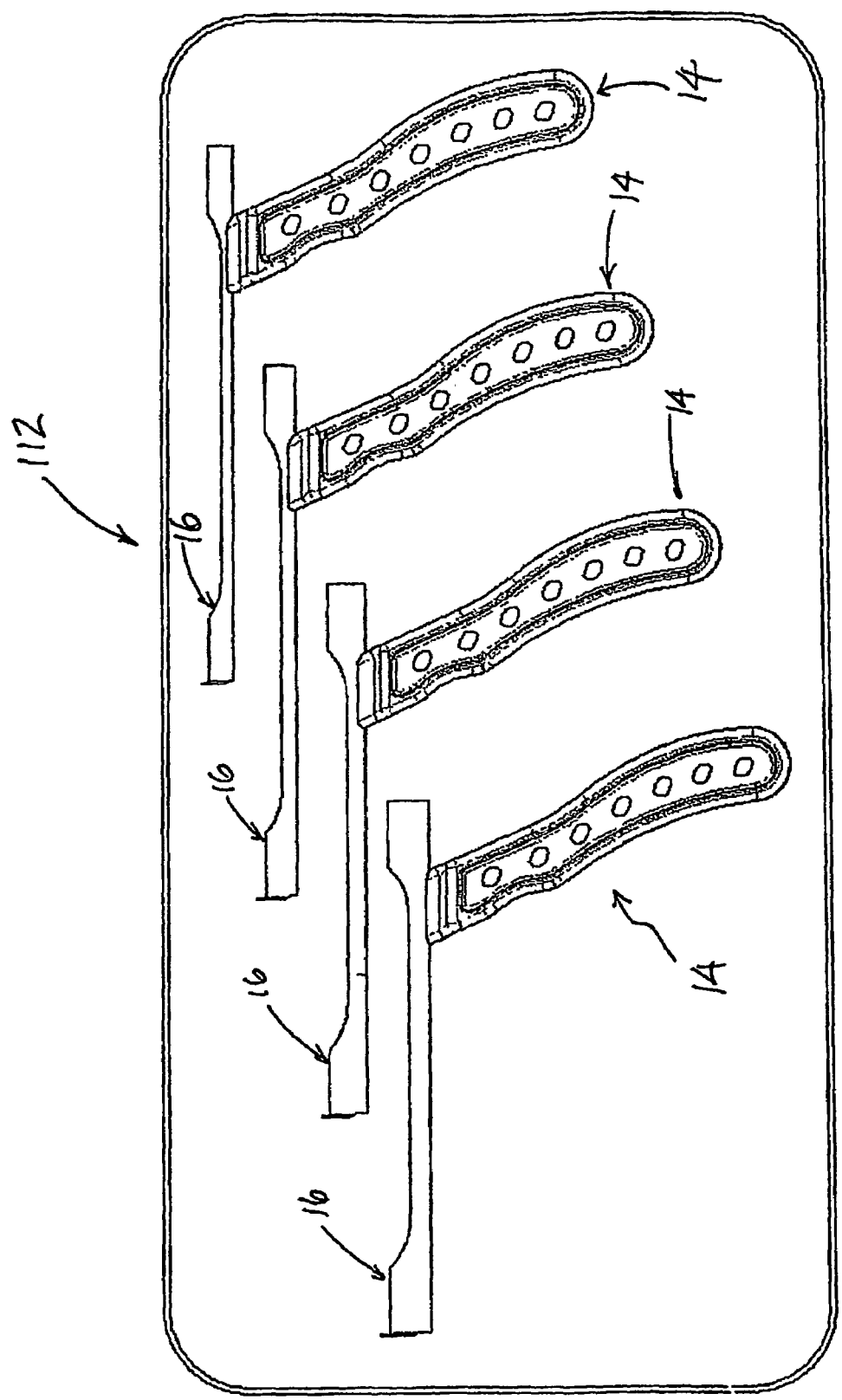

With reference to FIGS. 16-17, the tissue removal system 10 of the present invention may be provided in any number of suitable fashions, including the kit fashion shown comprising a first tray 110 and a second tray 112. By way of example only, the tray 110 may be provided having a plurality of brush members 12 of varying size and length to accommodate the particular surgical need or procedure. Tray 110 may also include components of the given drive mechanism, such as a pair of extension members 40 (for coupling to the quick coupling adapters 30 attached to the brush members 12), a pair of stopper assemblies 50, a handle assembly 51 (for quick-connect coupling to the extension member 40), and a pair of retractors 80 (in this embodiment, the fixed angle configuration). Tray 112 may include a plurality of cannula assemblies 14 having cannulas 16 with inner lumens having the same or similar diameters as the brush members 12 contained in tray 110. Providing the tissue removal system 10 of the present invention in this fashion is convenient and offers significant time savings and flexibility in tailoring the system 10 depending upon the given surgical procedures.

Figure 18:
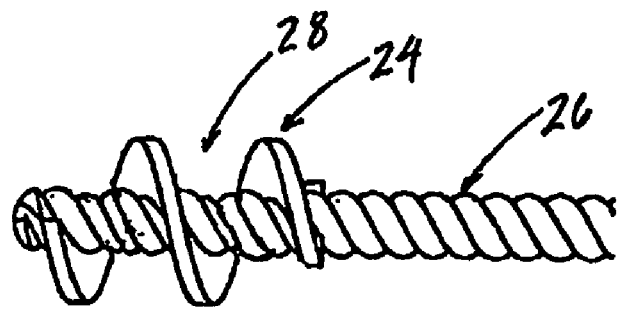
FIGS. 18-23 are side views showing various alternate configurations of the brush member according to the present invention.
Figure 19:
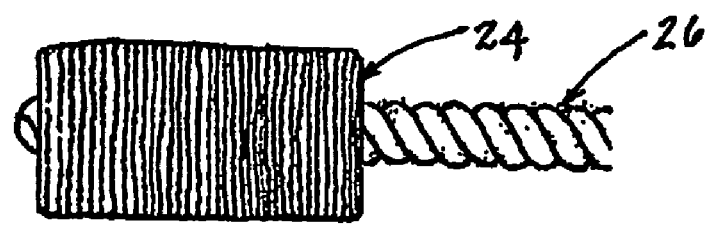
Figure 20:
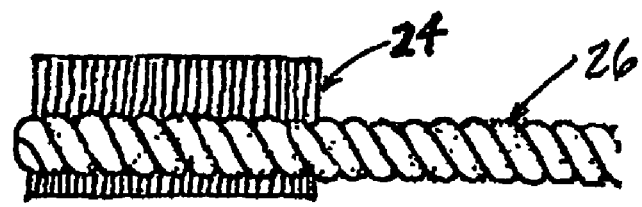
Figure 21:
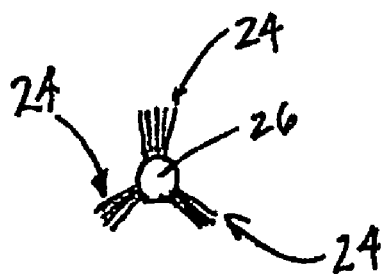
Figure 22:
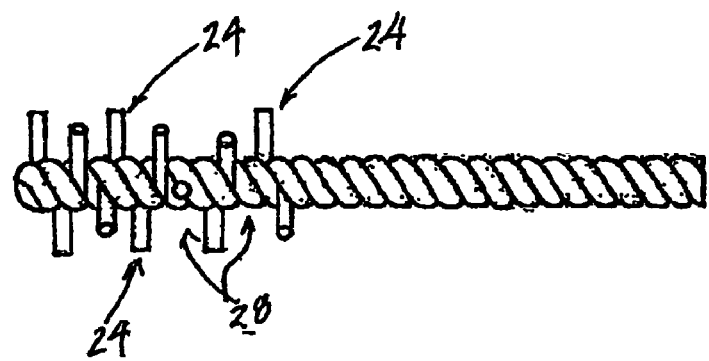
Figure 23:
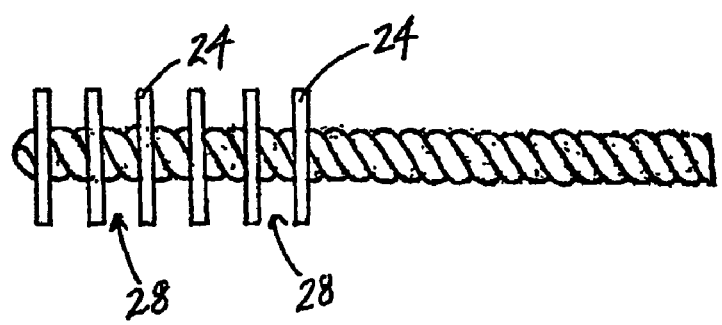
Figure 24:
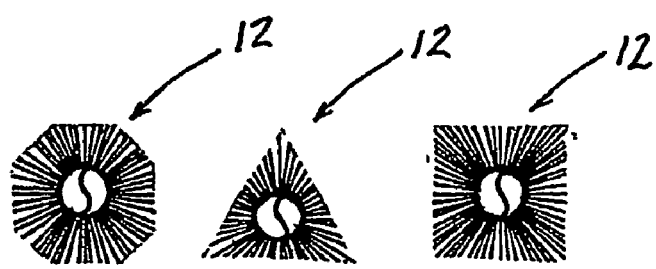
FIG. 24 are cross-sectional views illustrating several manners of providing the brush member.

As mentioned above, the brush member 12 forms an independent and significant feature of the present invention based on its capacity to carry body tissue both within the bristles of the brush, as well as between the groupings of bristles. Although shown above with reference to a dual spiral configuration, it is to be readily appreciated that the brush member 12 may be provided in any number of suitable fashions without departing from the scope of the present invention. For example, the brush member 12 may be provided having a single spiral bristle grouping 24 (see FIG. 18) defining a generally helical space 28 for receiving and carrying body tissue, a generally solid configuration (see FIG. 19) wherein the bristles have sufficient spacing therebetween to receive and carry body tissue, one or more radially extending bristle groupings 24 (FIGS. 20-21) defining at least one generally arcuate space 28 for receiving and carrying body tissue, and one or more axially disposed bristle groupings 24 (FIGS. 22-23) defining at least one generally axial space 28 for receiving and carrying body tissue. Moreover, the cross-sectional shape of the brush member 12 may vary from the generally circular cross-section of the cylindrical brush member 12 shown above, to any of a variety of polygonal cross-sections, including but not limited to those shown in FIG. 24.

Figure 25:
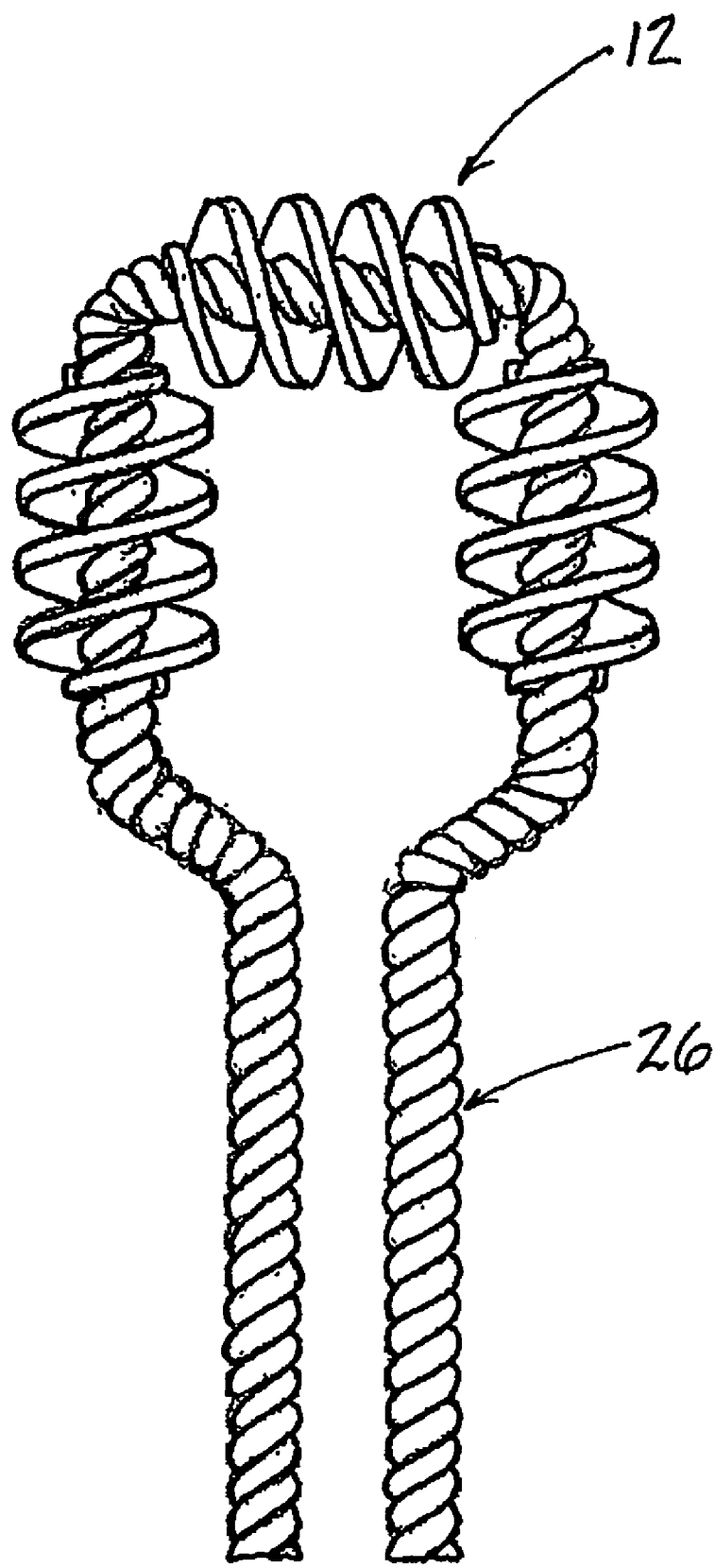
FIG. 25 is a top view of an alternate brush member configuration, disposed long a curved stem member.
Figure 26:
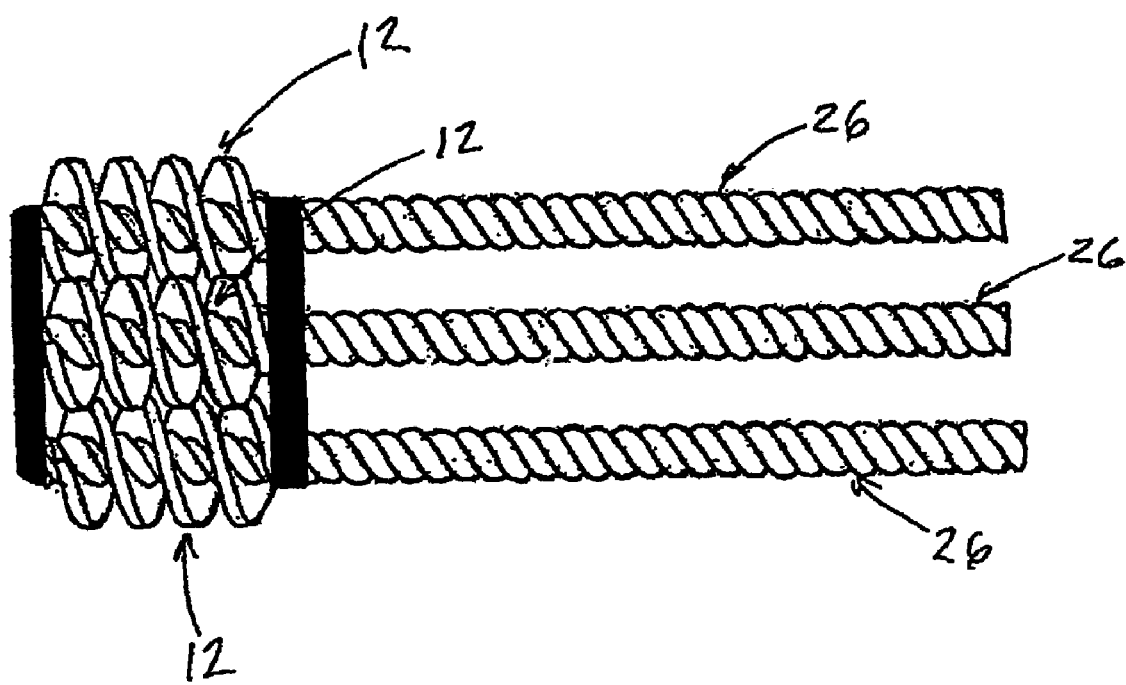
FIG. 26 is a top view of an alternate embodiment having multiple brush members and multiple stem members.

In a further aspect of the present invention, it is contemplated that the bristles forming the brush member 12 may be retractable toward the stem member 26 allowing for the brush diameter to be increased after insertion into the material to be excised. That feature may be accomplished by construction of the brush portion 11 from a material such as Nitinol or other "memory metal" or through a mechanical or electro-mechanical mechanism. It is similarly contemplated to (as shown in FIG. 25) provide the brush member 12 formed along a curved (or possibly rounded) stem member 26 for manual or automated manipulation within the target site (such as back-and-forth and/or side-to-side), as well as (as shown in FIG. 26) provide a plurality of brush members 12, each having a stem member 26 capable of independent manipulation (such as via rotation) and/or unison operation (moving the entire configuration back-and-forth and/or side-to-side) to effectuate body tissue removal.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined by the appended claims.

We claim:

1. A method for removing intervertebral disc material, comprising the steps of:
    creating a working channel from a patient's skin to an intervertebral disc space;
    providing a protector, said protector having a longitudinal axis and including retractor having first and second generally rectangular, planar blade members fixed in position relative to one another to form a generally V-shaped construct for establishing a barrier, said construct having a longitudinal axis extending in a generally parallel orientation relative to said longitudinal axis of said protector;
    positioning said protector near an entrance into said intervertebral disc space between said working channel and at least two of neural tissue, dura tissue, and vasculature adjacent to said entrance such that said first blade member prevents neural tissue from migrating into said working channel, and said second blade member prevents at least one of dura tissue and vasculature from migrating into said channel;
    inserting a brush member through the working channel into said intervertebral disc space, said brush member having a length ranging from 0.25 to 4.0 inches, a diameter ranging from 0.082 to 1.225 inches, and a plurality of bristle members disposed in a helical configuration defining a capacity for carrying intervertebral disc material wherein said protector prevents contact between said brush member, said neural tissue and said at least one of dura tissue and vasculature;
    manipulating said brush member within said intervertebral disc space to receive intervertebral disc material within said brush member; and
    removing said brush member from said intervertebral disc space.

2. The method of claim 1, wherein said step of creating a working channel to the intervertebral disc space is accomplished via at least one of percutaneous surgical procedure and an open surgical procedure.

3. The method of claim 1, wherein said protector further comprises a cannula dimensioned to extend to said entrance of said intervertebral disc space, said cannula having an inner lumen dimensioned to slideably receive said brush member for passage into said intervertebral disc space.

4. The method of claim 3, wherein said cannula includes a lip member at a distal end thereof dimensioned to retract at least one of said neural tissue, dura tissue, and vasculature adjacent to said spine.

5. The method of claim 3, wherein said inner lumen of said cannula and said brush member have approximately the same cross-sectional shape.

6. The method of claim 1, wherein said brush member includes a stem member, and further including the step of providing a drive assembly capable of engaging with said stem member for manipulating said brush member within said intervertebral disc space.

7. The method of claim 6, wherein said drive assembly comprises one of a powered drive assembly coupled to said stem member and a manual drive assembly coupled to said stem member.

8. The method of claim 7, wherein said powered drive assembly is a power drill.

9. The method of claim 7, wherein said manual drive assembly includes a handle member capable of being coupled to said stem member.

10. The method of claim 9, wherein said manual drive assembly includes an extension member coupled to said handle and a quick-connect coupling assembly for releasable connection to said stem member.

11. The method of claim 7, wherein said drive assembly includes a stop member coupled to said stem member for controlling the depth to which said brush member can be advanced into said intervertebral disc space.

* * * * *